US006694334B2

(12) United States Patent
DuLong et al.

(10) Patent No.: US 6,694,334 B2
(45) Date of Patent: Feb. 17, 2004

(54) METHOD AND APPARATUS FOR DISPLAYING MEDICATION INFORMATION

(75) Inventors: Donna B. DuLong, Del Mar, CA (US); Steven R. Wehba, Carlsbad, CA (US); Douglas W. Comer, Oceanside, CA (US); Joanne S. Stark, San Diego, CA (US); Michael A. Kurtz, San Diego, CA (US); Barbara Trohimovich, San Diego, CA (US)

(73) Assignee: Bridge Medical, Inc., Solana Beach, CA (US)

( * ) Notice: Subject to any disclaimer, the term of this patent is extended or adjusted under 35 U.S.C. 154(b) by 0 days.

(21) Appl. No.: 10/386,087

(22) Filed: Mar. 11, 2003

(65) Prior Publication Data

US 2003/0172081 A1 Sep. 11, 2003

Related U.S. Application Data

(63) Continuation of application No. 09/815,479, filed on Mar. 23, 2001, now Pat. No. 6,542,902.

(60) Provisional application No. 60/191,955, filed on Mar. 24, 2000.

(51) Int. Cl.[7] .................................................. G06F 17/30

(52) U.S. Cl. ........................................ 707/104.1; 707/10

(58) Field of Search ........................... 707/104.1, 2, 10; 705/3; 221/13; 424/275.1; 600/300

(56) References Cited

U.S. PATENT DOCUMENTS 4,164,320 A 8/1979 Irazoqui et al. ............. 235/375
4,476,381 A 10/1984 Rubin ........................ 235/375
4,636,950 A 1/1987 Caswell et al. ............. 364/403
4,696,671 A 9/1987 Epstein et al. ................ 604/67
4,810,243 A 3/1989 Howson ...................... 604/31
4,828,545 A 5/1989 Epstein et al. ................ 604/66
4,831,562 A 5/1989 McIntosh et al. ........... 364/569
4,835,372 A 5/1989 Gombrich et al. .......... 235/375
4,839,806 A 6/1989 Goldfischer et al. ... 364/413.02
4,847,764 A 7/1989 Halvorson ............. 364/413.02
4,853,521 A 8/1989 Claeys et al. ............... 235/375
4,857,713 A 8/1989 Brown ....................... 235/375
4,857,716 A 8/1989 Gombrich et al. .......... 340/712
4,865,584 A 9/1989 Epstein et al. ................ 604/67
4,916,441 A 4/1990 Gombrich .................. 235/462
4,925,444 A 5/1990 Orkin et al. .................. 604/80
4,978,335 A 12/1990 Arthur, III ................... 604/67
5,006,699 A 4/1991 Felkner et al. .............. 235/472
5,036,852 A 8/1991 Leishman ................... 128/630
5,072,383 A 12/1991 Brimm et al. ......... 364/413.02
5,088,981 A 2/1992 Howson et al. ............... 604/31
5,100,380 A 3/1992 Epstein et al. ................ 604/67
5,153,416 A 10/1992 Neeley ....................... 235/375
5,153,827 A 10/1992 Coutré et al. .......... 364/413.02
5,207,642 A 5/1993 Orkin et al. .................. 604/65
5,256,157 A 10/1993 Samiotes et al. ........... 604/246

(List continued on next page.)

*Primary Examiner*—Diane D. Mizrahi
(74) *Attorney, Agent, or Firm*—Gates & Cooper LLP

(57) ABSTRACT

A method, system, and article of manufacture for ensuring that the content and appearance of medication information is consistent, accurate, and reliable across multiple hospitals, sites, and users. Publicly available databases provide medication information. Relevant data is extracted from such databases and placed into a drug reference table. The drug reference table is combined with a hospital formulary such that the medication information in the formulary is modified, completed, reformatted, etc. Such modifications, completions, and reformatting are conducted by enforcing one or more rules that are applied to elements and attributes of a medication. The resulting medication information content is stored in a hospital formulary file that is accessed and utilized for maintaining, displaying, administering, etc. medication. To combine the drug reference table with the formulary, a hospital setup tool comprising a graphical user interface that allows a user to approve and finalize medication information may be utilized.

30 Claims, 5 Drawing Sheets

DATABASE 202
EXTRACT
RELEVANT DATA 204
DRUG REFERENCE TABLE 206
INPUT
PHARMACY FORMULARY 208
INPUT
HST 210
HFF 212

U.S. PATENT DOCUMENTS 5,265,010 A 11/1993 Evans-Paganelli et al. ..................... 364/413.02
5,267,174 A 11/1993 Kaufman et al. ........... 364/479
5,317,506 A 5/1994 Coutré et al. .......... 364/413.02
5,374,813 A 12/1994 Shipp ......................... 235/375
5,390,238 A 2/1995 Kirk et al. .................... 379/93
5,416,695 A 5/1995 Stutman et al. ........ 364/413.02
5,431,450 A 7/1995 Coleman ..................... 283/62
5,536,084 A 7/1996 Curtis et al. ........... 364/413.01
5,594,786 A 1/1997 Chaco et al. ................. 379/93
5,608,904 A 3/1997 Chaudhuri et al. ............ 707/2
5,700,998 A 12/1997 Palti ........................... 235/375
5,713,856 A 2/1998 Eggers et al. ................. 604/68
5,758,095 A 5/1998 Albaum et al. ................ 705/2
5,781,442 A 7/1998 Engleson et al. ...... 364/478.02
5,800,387 A 9/1998 Duffy et al. .................. 604/65
5,836,910 A 11/1998 Duffy et al. .................. 604/65
5,845,255 A * 12/1998 Mayaud ......................... 705/3
5,924,074 A 7/1999 Evans ........................... 705/3
6,032,119 A 2/2000 Brown et al. ............... 235/456
6,032,861 A 3/2000 Lemelson et al. .......... 235/456
6,421,650 B1 7/2002 Goetz et al. ................... 705/3
6,471,089 B2 * 10/2002 Liff et al. ..................... 221/13
6,482,156 B2 * 11/2002 Iliff ............................ 600/300
6,555,116 B1 * 4/2003 Buchanan et al. ....... 424/275.1
6,581,798 B2 * 6/2003 Liff et al. ..................... 221/13
2002/0035484 A1 3/2002 McCormick ................... 705/2

Figure 4:
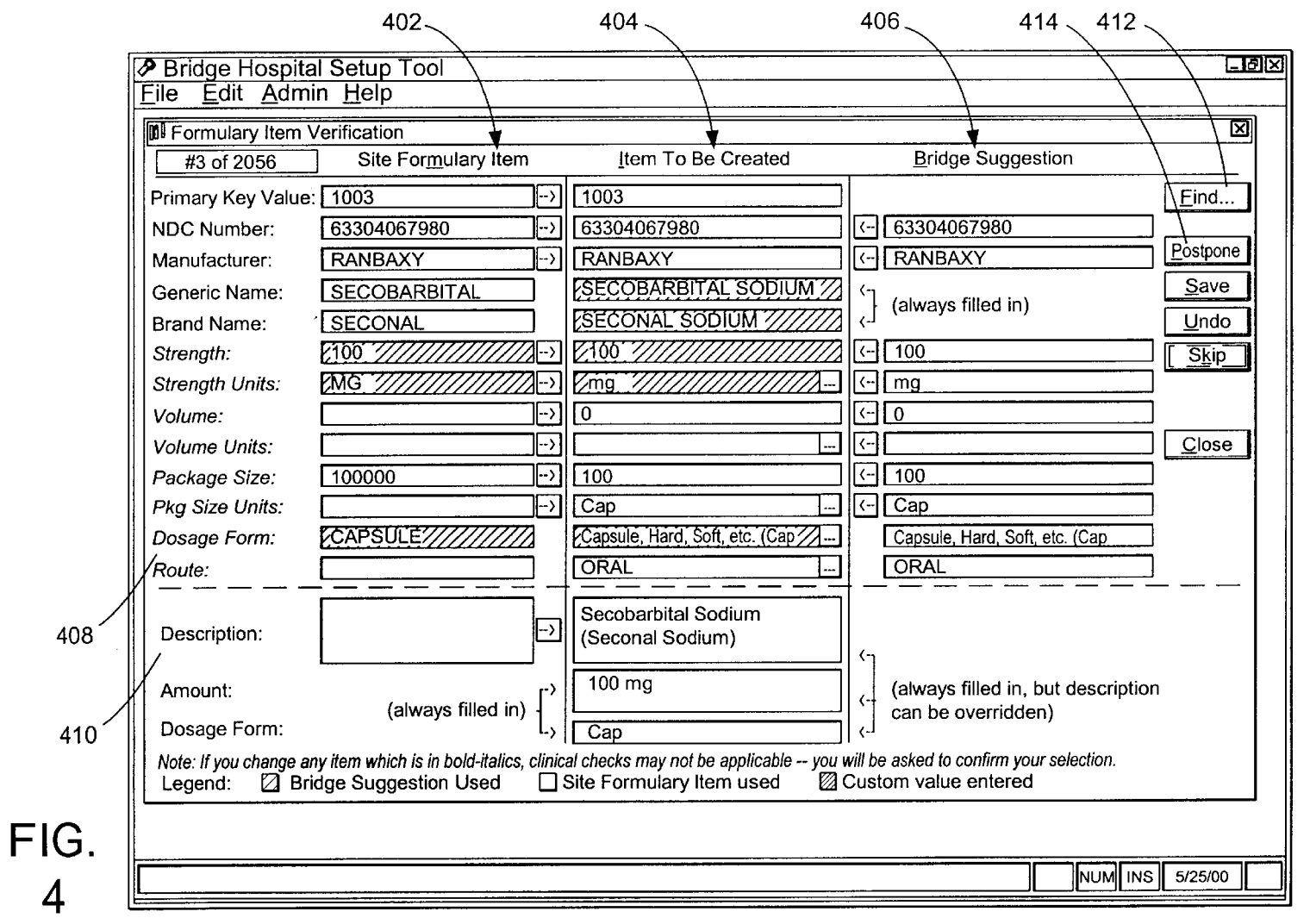

* cited by examiner 402
404
406
414
412

Bridge Hospital Setup Tool

File Edit Admin Help

Formulary Item Verification

| #3 of 2056 | Site Formulary Item | Item To Be Created | Bridge Suggestion |
| --- | --- | --- | --- |
| Primary Key Value: | 1003 | 1003 | |
| NDC Number: | 63304067980 | 63304067980 | 63304067980 |
| Manufacturer: | RANBAXY | RANBAXY | RANBAXY |
| Generic Name: | SECOBARBITAL | SECOBARBITAL SODIUM | (always filled in) |
| Brand Name: | SECONAL | SECONAL SODIUM | |
| *Strength:* | 100 | 100 | 100 |
| *Strength Units:* | MG | mg | mg |
| *Volume:* | | 0 | 0 |
| *Volume Units:* | | | |
| *Package Size:* | 100000 | 100 | 100 |
| *Pkg Size Units:* | | Cap | Cap |
| *Dosage Form:* | CAPSULE | Capsule, Hard, Soft, etc. (Cap | Capsule, Hard, Soft, etc. (Cap |
| *Route:* | | ORAL | ORAL |
| Description: | | Secobarbital Sodium (Seconal Sodium) | (always filled in, but description can be overridden) |
| Amount: | (always filled in) | 100 mg | |
| Dosage Form: | | Cap | |

Find...
Postpone
Save
Undo
Skip
Close

*Note: If you change any item which is in bold-italics, clinical checks may not be applicable -- you will be asked to confirm your selection.*

Legend: Bridge Suggestion Used Site Formulary Item used Custom value entered

NUM INS 5/25/00

Figure 5:
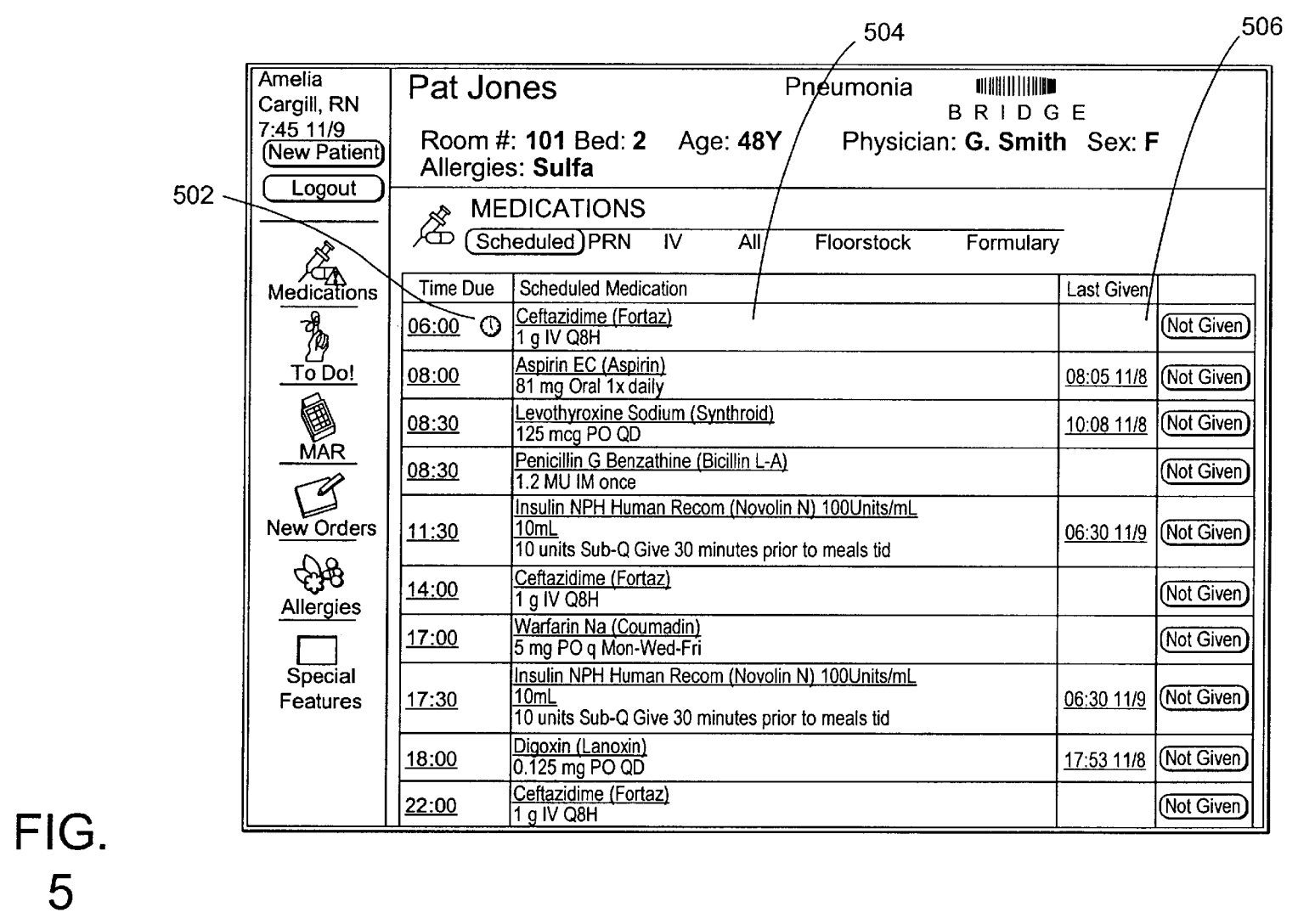

Amelia
Cargill, RN
7:45 11/9
New Patient
Logout

Medications
To Do!
MAR
New Orders
Allergies
Special Features

Pat Jones    Pneumonia    BRIDGE
Room #: 101 Bed: 2    Age: 48Y    Physician: G. Smith    Sex: F
Allergies: Sulfa

MEDICATIONS
Scheduled  PRN  IV  All  Floorstock  Formulary

| Time Due | Scheduled Medication | Last Given | |
|---|---|---|---|
| 06:00 | Ceftazidime (Fortaz)<br>1 g IV Q8H | | Not Given |
| 08:00 | Aspirin EC (Aspirin)<br>81 mg Oral 1x daily | 08:05 11/8 | Not Given |
| 08:30 | Levothyroxine Sodium (Synthroid)<br>125 mcg PO QD | 10:08 11/8 | Not Given |
| 08:30 | Penicillin G Benzathine (Bicillin L-A)<br>1.2 MU IM once | | Not Given |
| 11:30 | Insulin NPH Human Recom (Novolin N) 100Units/mL<br>10mL<br>10 units Sub-Q Give 30 minutes prior to meals tid | 06:30 11/9 | Not Given |
| 14:00 | Ceftazidime (Fortaz)<br>1 g IV Q8H | | Not Given |
| 17:00 | Warfarin Na (Coumadin)<br>5 mg PO q Mon-Wed-Fri | | Not Given |
| 17:30 | Insulin NPH Human Recom (Novolin N) 100Units/mL<br>10mL<br>10 units Sub-Q Give 30 minutes prior to meals tid | 06:30 11/9 | Not Given |
| 18:00 | Digoxin (Lanoxin)<br>0.125 mg PO QD | 17:53 11/8 | Not Given |
| 22:00 | Ceftazidime (Fortaz)<br>1 g IV Q8H | | Not Given |

METHOD AND APPARATUS FOR DISPLAYING MEDICATION INFORMATION

CROSS-REFERENCE TO RELATED APPLICATIONS

This application claims the benefit under 35 U.S.C. Section 120 of the following commonly-assigned U.S. utility patent application, which is incorporated by reference herein:

Utility Application Ser. No. 09/815,479, filed Mar. 23, 2001, by Donna B. Dulong, Steven R. Wehba, Douglas W. Comer, Joanne S. Stark, Michael A. Kurtz, and Barbara Trohimovich, entitled "METHOD AND APPARATUS FOR DISPLAYING MEDICAL INFORMATION," now U.S. Pat. No. 6,542,902, issued Apr. 6, 2003, which application claims the benefit under 35 U.S.C. § 119(e) of U.S. provisional application Ser. No. 60/191,955, entitled "SYSTEM AND METHOD FOR AUTOMATING MEDICATION ERROR DETECTION AND PREVENTION," filed on Mar. 24, 2000, by Donna B. Dulong, et. al., which application is incorporated by reference herein.

BACKGROUND OF THE INVENTION

1. Field of the Invention

The present invention relates generally to the prevention of errors in medication administration, and in particular, to a method, apparatus, system, and article of manufacture for consistently displaying medication information.

2. Description of the Related Art

The proliferation of new drugs and increasing complexity of drug therapy has dramatically increased the incidence of medication errors and adverse drug events in hospitals. With the aging of the population, hospitals are treating more elderly and acutely ill patients whose ability to tolerate medication errors is compromised. At the same time, economic pressure from managed care and reduced reimbursement rates from public and private payors have caused hospitals to increase the patient/nurse ratio.

The process for administering drugs to patients has changed little in the past two decades. The process typically relies on verbal and written communication and involves several different clinicians from various areas within a hospital. Medication errors occur at every stage of the medication use process—in physician prescribing, order transcription, drug preparation, drug dispensing, and in administration to the patient. Existing information systems and automated drug distribution systems only incidentally address the problem of medication errors.

Several recent studies have documented the alarming rate of medication errors and adverse drug reactions in hospitals and their resulting deaths and related costs. Some of the findings are as follows:

- 6.5% of patients will experience a potentially serious error while hospitalized
- over $4.0 billion in additional hospital costs are caused by medication errors and adverse drug events Recently, the awareness of the high level of medication errors within hospitals has increased significantly and many leading hospitals in the United States have experienced highly publicized cases related to catastrophic medical errors. Lawsuits associated with medication errors have proliferated. In addition to the legal costs, hospitals' institutional reputations may be at risk if there is a highly publicized patient death due to medication error.

In response to the growing risks of medication errors, leading hospitals have developed initiatives to focus on the issue. In addition, professional associations representing nurses, hospital pharmacists, and physicians have identified medication errors as a major issue. The Health Care Finance Administration (HCFA) has discussed regulations that would exclude hospitals with high rates of medication error from reimbursement under the Medicare program. As a result, many constituencies are seeking a standard of care within hospitals to address the problem of medication errors and adverse drug events.

A significant cause of medication error results from the inconsistent display and interpretation of medication information. Inconsistent displays and interpretations may arise at numerous stages in the processing and administration of medication including prescription interpretation, prescription order transcription and entry, medication dispensing (at a pharmacy), medication retrieval (by a nurse), medication administration, etc.

For example, a doctor may desire to write a prescription for 100 10 milligram tablets of medicine XYZ to be delivered orally 2 times a day. However, when writing the prescription, the doctor may write medicine XYZ using an abbreviation (e.g., X), with a dosage of 100.0 without indicating the dosage unit (e.g., mg (milligram) or μg (microgram)) or dosage schedule/frequency (e.g., 2 times daily), and may fail to indicate the method of administration (e.g., oral). Such a prescription may not be consistently interpreted. For example, when entering the prescription into a computer system, the pharmacist may omit some of the missing important information, wrongly interpret the abbreviation, enter the information using abbreviations different from that used in the prescription (i.e., those used in the pharmacy's own formulary), further abbreviate the remaining medication information (e.g., ×2 for two times daily), or incorrectly indicate a dosage of 1000 micrograms to be taken three times a day. Further errors may occur when the prescription is filled by another pharmacist that may interpret the information in the computer (e.g., the abbreviations) differently, when a nurse misinterprets the computer display of the prescription and obtains the wrong medication from floorstock, or when a nurse administers the medication and misinterprets the information.

Individual hospitals and pharmacies often use different abbreviations/formularies for medication information. Consequently, when personnel move from one hospital/pharmacy to another, there is a high likelihood that the personnel will misinterpret the medication information. Additionally, the medication information (and abbreviations) used on a prescription label may differ from the medication information displayed on the computer or on a medical administration record (MAR) that is used to record the status and treatment of a patient. Such differences may result in a medication error during the administration of the medication.

What is needed is the ability to consistently display and store medication information such that fewer errors are made when interpreting the information in a computer or on a MAR. Additionally, what is needed is a consistent and complete display of medication information across multiple sites.

SUMMARY OF THE INVENTION

A method and apparatus for consistently and accurately displaying medication information. Medication errors result in a significant number of injuries and deaths each year. One cause of medication errors includes the lack of consistence and reliability in the content and appearance of medication information. For example, different content for the same medication or the use of different abbreviations or terms when displaying the same medication may lead to the misinterpretation or improper use of a medication.

One or more embodiments of the invention provide a method, system, and article of manufacture for ensuring that the content and appearance of medication information is consistent, accurate, and reliable across multiple hospitals, sites, and users. Publicly available databases provide medication information. Relevant data is extracted from such databases and placed into a drug reference table.

Different hospitals and pharmacies maintain internal formularies that store and provide access to medication information provided by the hospital/pharmacy. Such information is often incomplete, inconsistent, and varies from hospital to hospital.

The drug reference table is combined with the formulary such that the medication information in the formulary is modified, completed, reformatted, etc. Such modifications, completions, and reformatting are conducted by enforcing one or more rules that are applied to elements and attributes of a medication. For example, rules may cause the conversion of a “T” in the formulary file to “TAB” to indicate a medication’s route of administration. Similarly, leading or trailing zeroes may be removed, measurement unit abbreviations may be expanded or adjusted, capitalization may be adjusted, etc.

The resulting medication information content is stored in a hospital formulary file that is accessed and utilized for maintaining, displaying, administering, etc. medication.

To combine the drug reference table with the formulary, a hospital setup tool may be utilized. The hospital setup tool provides a graphical user interface with several columns. One column presents medication information from the formulary. A second column presents suggested medication information from the drug reference table. The suggested medication information is obtained by attempting to match the formulary information with relevant fields in the drug reference table. For example, if the national drug code (NDC) information stored in the formulary matches a NDC number from the drug reference table, the appropriate medication information is retrieved and displayed in the second column.

A third column presents the final medication information to be utilized in the hospital formulary file. Such final medication information may include a medication display description that will be used when the medication is displayed. The medication display description comprises multiple elements of a medication and may be adjusted by the user, if desired. For example, the medication display description may comprise a generic or brand display name of the medication (e.g., Morphine), followed by the strength and strength units (e.g., 200 mG).

Accordingly, a completed hospital formulary file reflects accurate and consistent medication information that the individual pharmacy or hospital has approved. Such medication information may then be utilized and displayed in a consistent manner to prevent medication errors. For example, all of the scheduled medications for a given patient may consistently display appropriate medication information for each patient order. Such information may include the medication display description and the dosage and route of administration information.

BRIEF DESCRIPTION OF THE DRAWINGS

Referring now to the drawings in which like reference numbers represent corresponding parts throughout:

FIG. 4 illustrates a graphical user interface utilized in mapping medication information between a hospital/pharmacy formulary and a drug reference table in accordance with one or more embodiments of the invention; and FIG. 5 illustrates a graphical user interface displaying scheduled medications in accordance with one or more embodiments of the invention.

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

A medication management system utilizes display rules that provide medication descriptive information that is accurate, consistent in appearance and easily recognized by system users and capable of being sorted in a manner that ensures users have visibility to all medications within either a selected generic or brand-name group. Descriptive information that is controlled and managed in this manner contributes to the overall medication management system goal of reducing, if not eliminating, potential medication errors at a patient’s bedside.

Hardware Environment

Figure 1:
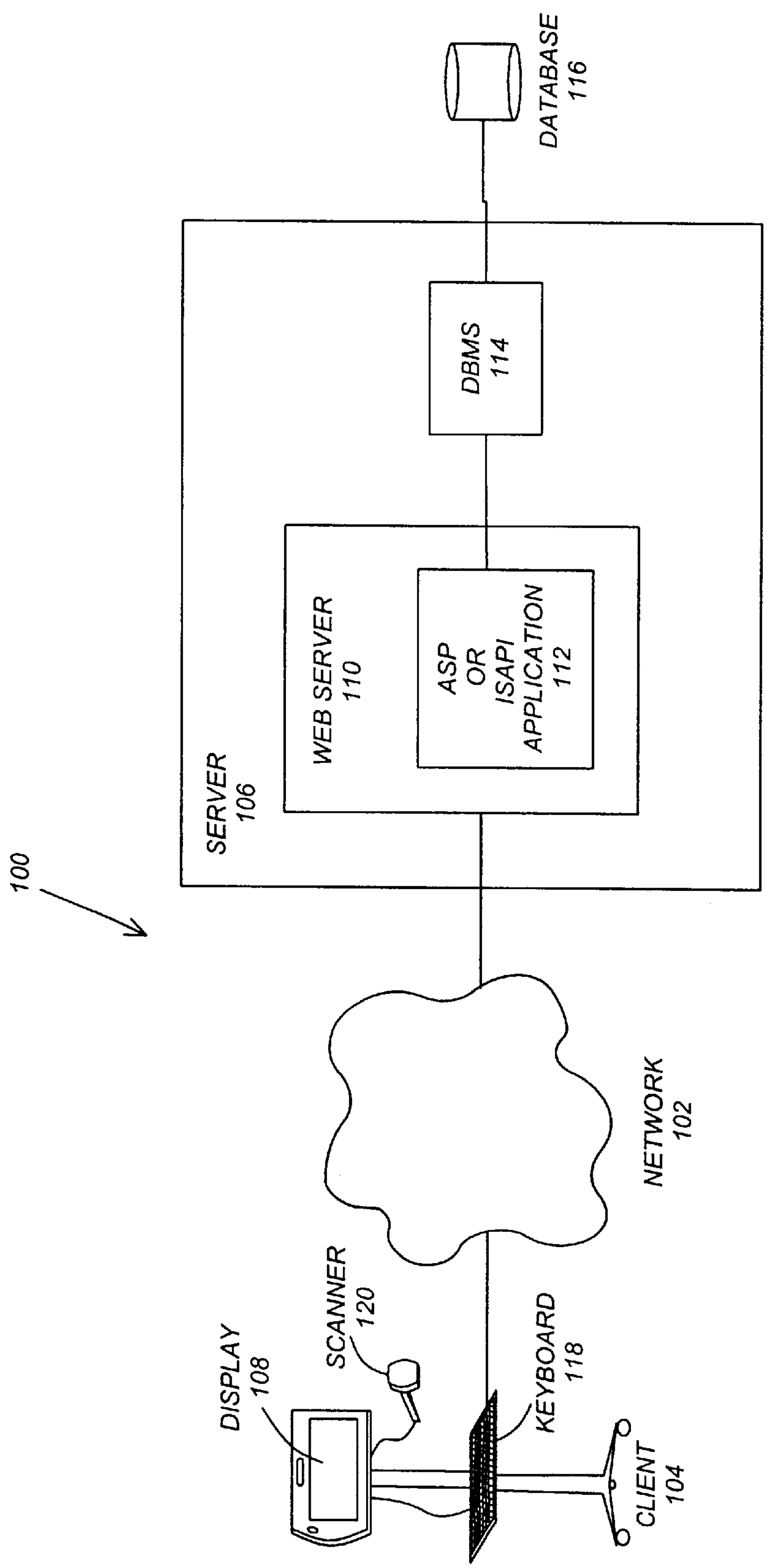
FIG. 1 schematically illustrates a hardware and software environment in accordance with one or more embodiments of the invention.

FIG. 1 schematically illustrates a hardware and software environment in accordance with one or more embodiments of the invention, and more particularly, illustrates a typical distributed computer system 100 using a network 102 to connect client systems 104 at a client 104 bedside to server computers 106. A typical combination of resources may include a network 102 comprising an intranet, the Internet, LANs, WANs, SNA networks, or the like, clients 104 operating/used at a client’s 104 bedside that are personal computers, workstations, pen tablets, Windows CE devices, etc., and servers 106 that are personal computers, workstations, minicomputers, mainframes, etc. Additionally, client 104 and server 106 may receive input using a touch pad display 108, keyboard 118, bar code scanner 120, cursor control device, or other input device.

In accordance with one or more embodiments of the invention, a network 102 such as the Internet or a hospital intranet connects clients 104 to server computers 106. Additionally, network 102 may utilize radio frequency (RF) to connect and provide the communication between clients 104 and servers 106. Clients 104 may execute a client application or Web browsers on display 108 and communicate with server computers 106 executing Web servers 110. Such a Web browser is typically a program such as NETSCAPE NAVIGATOR or MICROSOFT INTERNET EXPLORER. Further, the software executing on clients 104 may be downloaded from server computer 106 to client computers 104 and installed as a plug in or ActiveX control of a Web browser. Accordingly, clients 104 may utilize ActiveX components/component object model (COM) or distributed COM (DCOM) components to provide a user interface or presentation layer on display 108. The Web server 110 is typically a program such as IBM's HyperText Transport Protocol (HTTP) Server or Microsoft's Internet Information Server. Thus, server 106 provides business logic to control a system of the invention and to communicate with client 104.

In one or more embodiments of the invention, web server 110 hosts an Active Server Page (ASP) or Internet Server Application Programming Interface (ISAPI) application 112, which may be executing scripts. The scripts invoke objects that execute business logic (referred to as business objects). The business objects then manipulate data in database 116 through a database management system (DBMS) 114. When a developer encapsulates the business functionality into objects, the system may be referred to as a component object model (COM) system. Accordingly, the scripts executing on web server 110 (and/or application 112) invoke COM objects that implement the business logic. Further, server 106 may utilize Microsoft's Transaction Server (MTS) to access required data stored in database 116 via an interface such as ADO (Active Data Objects), OLE DB (Object Linking and Embedding DataBase), or ODBC (Open DataBase Connectivity).

Generally, these components 108–120 all comprise logic and/or data that is embodied in or retrievable from device, medium, signal, or carrier, e.g., a data storage device, a data communications device, a remote computer or device coupled to the computer via a network or via another data communications device, etc. Moreover, this logic and/or data, when read, executed, and/or interpreted, results in the steps necessary to implement and/or use the present invention being performed.

Thus, embodiments of the invention may be implemented as a method, apparatus, or article of manufacture using standard programming and/or engineering techniques to produce software, firmware, hardware, or any combination thereof. The term "article of manufacture" (or alternatively, "computer program product") as used herein is intended to encompass logic and/or data accessible from any computer-readable device, carrier, or media.

Those skilled in the art will recognize many modifications may be made to this exemplary environment without departing from the scope of the present invention. For example, those skilled in the art will recognize that any combination of the above components, or any number of different components, including different logic, data, different peripherals, and different devices, may be used to implement the present invention, so long as similar functions are performed thereby.

Software Embodiments

A software product used primarily by nurses and other healthcare professionals in a hospital setting may be utilized in accordance with embodiments of the invention. The software product enables hospitals to reduce medication errors by electronically verifying at the patient bedside, the "five rights" (right patient, right drug, right dose, right route of administration, and right time) before the drug is administered to the patient. Additionally, the software product may provide for the electronic verification of the compliance/violation of multiple additional compliance rules maintained by the system or entered by a user. The compliance rules provide for the verification of medication administration well beyond the traditional "five rights". The system also provides valuable and comprehensive medication information needed to continually improve the safety and quality of the hospital's medication management system and patient outcomes.

Multiple pharmacies and hospitals construct a formulary that is used to represent and store medication information. Since different formularies are constructed by multiple pharmacies over time, the medication information is not represented consistently. Thus, different pharmacies/hospitals utilize different formularies and the data and abbreviations therein to represent the same medication. Such inconsistencies are a significant cause of medication error.

To reduce or prevent medication errors resulting from these inconsistencies, one or more embodiments of the invention utilize various components that are collectively referred to as display rules that provide medication description information that is accurate, consistent in appearance and easily recognized by system users. Such display rules also provide the capability for the medication description information to be sorted in a manner that ensures users have visibility to all medications within either a selected generic or brand-name group. Descriptive information that is controlled and managed in this manner contributes to the overall system of reducing, if not eliminating, potential medication errors at the bedside.

For example, if the dosage form in a formulary is "TAB", one or more display rule components may provide for expanding the abbreviation into "TABLET". Similar display rule components may be utilized to convert medication names, dosage forms, dosage route, etc. Using such display rule components, different hospital formularies may all utilize a consistent format for medication information. Thus, there is consistency between physicians, nurses, and pharmacists with respect to writing, viewing, and administering orders. Further, by mapping/converting the medication information to a consistent format, data warehousing/mining of the medication information may more easily be performed. The usefulness of such data warehousing increases as the data is aggregated across multiple hospitals/pharmacies.

One or more of the following components form the basic structure utilized in accordance with one or more embodiments of the invention:

(1) Medication Description Management;

(2) Data Reconstruction;

(3) Element and Attribute Rules; and (4) Hospital Setup Tool.

Medication Description Management

Medication descriptions must provide information that is sufficiently detailed so that it is clearly identifiable as the "right drug". Part of that need is provided for by the description's content and part by its appearance. The medication description management component provides the overall structure and procedure that is utilized to ensure the accuracy and consistency of a medication description's content and appearance.

Figure 2:
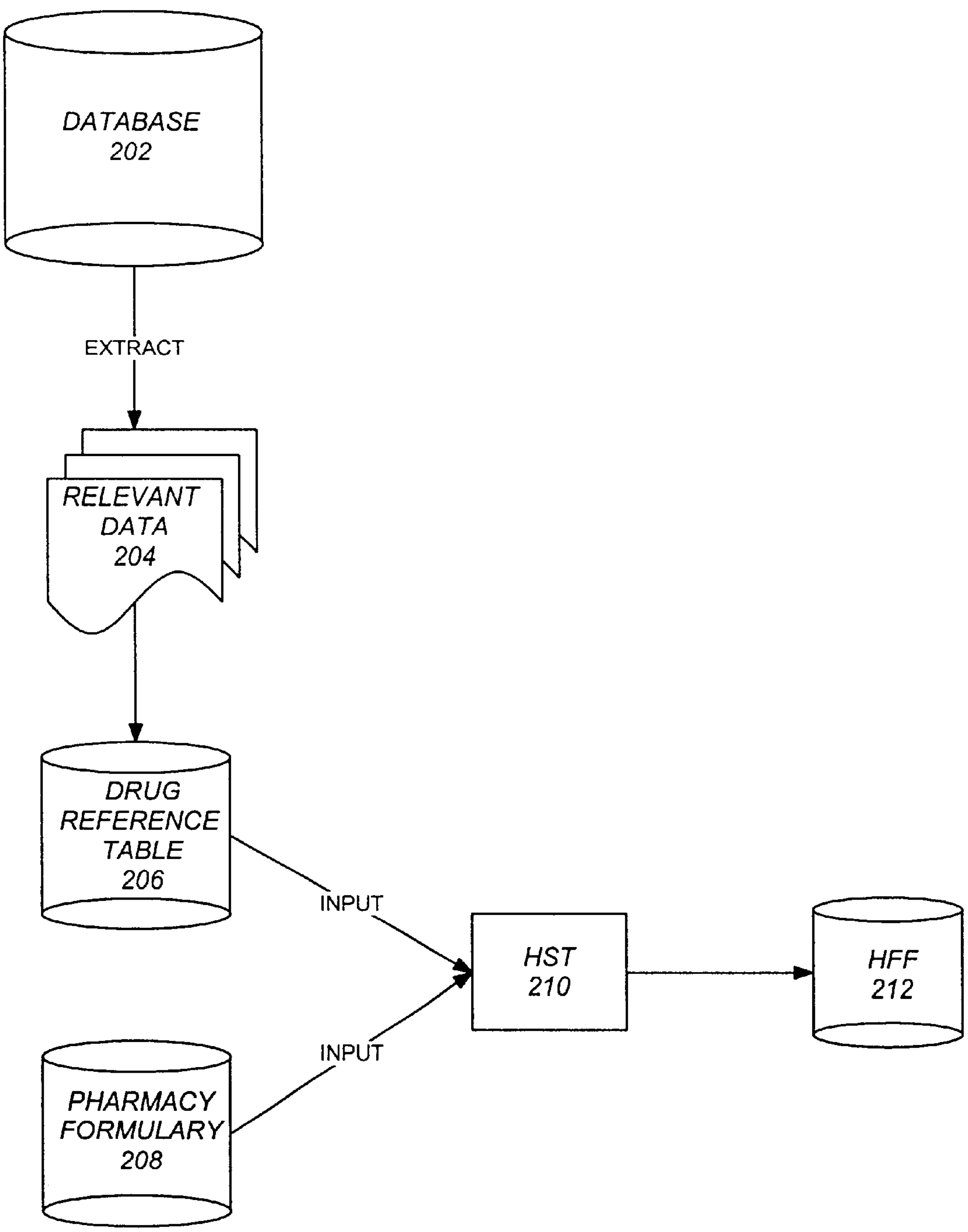
FIG. 2 illustrates the flow of information that enables the use and display of appropriate medication descriptions in accordance with one or more embodiments of the invention.

FIG. 2 illustrates the flow of information as provided by the medication description component in accordance with one or more embodiments of the invention. Third party providers such as First Data Bank, Multim, or Micromedix maintain databases 202 of the medications/drugs in existence (e.g., the NDDF (National Drug Data File) from First Data Bank). Such databases 202 include information such as medication names, dosage route, allergy-drug interactions, food-drug interactions, patient educational materials, etc. as published by the drug manufacturers and collected by the third party providers. Relevant data 204 from database 202 is extracted and input into a reference drug table 206. Accordingly, reference drug table 206 contains relevant organized medication information.

The reference drug table 206 is combined with a hospital's/pharmacy's internal formulary 208 and assembled using a hospital setup tool 210 (also referred to as the hospital formulary tool or display name manager tool) into a hospital formulary file (HFF) 212. The hospital setup tool 210 aids users in creating and providing consistent medication description content and appearance for storage in the hospital formulary file 212.

Accordingly, the content of a medication description and how that content appears/is displayed is generated from various elements that are gathered from both the reference drug table 206 and hospital formulary 208. Examples of the elements used (from both drug reference table 206 and pharmacy formulary 208) to create the medication description are display name, generic name, brand name, drug strength, package size, and dosage form. Various make-safe rules (see discussion below) are utilized to calculate a set of display-related elements of the medication description. The display-related elements, in turn, are used to construct a final displayed medication description by stringing together the display-related elements in a controlled manner that determines which of the display-related elements are to be used, and where the elements are to be used as part of a final displayable medication description.

Every medication is tested against a specified set of make-safe rules in order to construct its final medication description. The final medication description is then stored in the HFF 212 as an additional element. Thus, the drug reference table 206, pharmacy formulary 208, make-safe rules, and hospital setup tool 210 are utilized to create the final medication description from various elements that are eventually stored within the HFF 212.

Accordingly, the final medication description is provided by HFF 212, and used for display on display 108. The features that are utilized in the creation of the medication description and final medication description may be specified by the make-safe rules as described below.

Data Reconstruction

Although the database 202 or pharmacy formulary 208 may provide a significant amount of data, the databases 202 and 208 often cannot supply complete data that can be stored and managed in a system of the invention. For example, medications that have a combination of drugs of differing strengths do not show numerical data of the drug amounts. Further, many times, the strength units of the drugs are not provided. The system specifies how incomplete data is to be reconstructed based upon all of the available information provided by the database 202 and pharmacy formulary 208. The numerical data can be reconstructed into the drug reference table 206 or hospital formulary file 212 and indicate the "extrapolated units" or other missing information.

The data may be reconstructed based on the information provided. Accordingly, if the pharmacy formula 208 contains complete national drug code (NDC) information for a listed medication, data for the medication with the matching NDC is retrieved from the drug reference table 206. Additionally, the system may attempt to locate a matching medication in drug reference table 206 based on one or more fields/elements from pharmacy formulary 208. For example, if pharmacy formulary 208 contains a name and administration route, the medication with a matching name (generic or brand) and administration route will be attempted. Selected fields, from pharmacy formulary 208 may be utilized, preferred, or given precedence in attempting to locate a matching medication in drug reference table 206. Such precedence resolves inconsistencies with the data in pharmacy formulary 208.

Element and Attribute Rules

Element and attribute rules are applied to elements and attributes of a medication to ensure the medication maintains consistent and accurate content and appearance. The rules may be used to create new attributes and elements or to ensure the accuracy of information in existing attributes and elements.

A final medication description's content and appearance may be based upon various elements. One such element is a "display name" element. The "display name" element may have two forms: one display name based upon the medication's generic name, the other based upon its brand name (both of which are maintained in drug reference table 206). The purpose of having the two forms allows the medications to be sorted by either generic or brand name, thereby providing the user with an option if one of the names is known and not the other.

Element and attribute rules may be grouped into various categories focusing on specific aspects of the elements of a medication description as follows:

Make Safe Rules

As described above, the medication descriptions are based upon the generic and brand names extracted from database 202. After obtaining a display name for a medication, the name must be formatted for appropriate use and display. Make safe rules are utilized to format and adjust the medication descriptions for this purpose. Make safe rules provide for formatting the display names for easier reading and modifying the display names so that the reference drug table 206 acronyms, abbreviations, and typographical errors are transformed into full and complete terminologies that are consistent across the entire spectrum of all medications placed into HFF 212.

The make safe rules gather the data from various elements to ensure that detailed medication information is accurate and consistent. Make safe rules provide the ability for server 106 to create "safe" values for various drug attributes/elements, including proper spacing and special formatting. Accordingly, some "make safe" rules ensure that certain fields are in the proper format and contain the appropriate information. For example, when a "make safe" procedure is called, the procedure may ensure the proper format and information is maintained for drug strength units, drug strength volume units, max daily dose units, etc.

A single "make safe" procedure may be utilized in accordance with one or more embodiments of the invention. When the single "make safe" procedure is called, the caller includes the attributes/elements to make safe as parameters of the function call. The "make safe" procedure returns a value that has been made "safe".

Units of Measurement Rules

One or more make safe rules may be applied to elements related to the units of measurement (UOM) for the medications. A UOM specifies the unit utilized to quantify and measure the medication. For example, a UOM may be Billion Units, mL, mm, 1000, etc. A UOM may comprise a string component and a numerical value component. For example, the UOM string component may be gram or G, and the UOM numerical value component may be 1,000,000, 1,000, etc.

Make safe rules that are UOM (referred to as UOM rules) related ensure that both the string and numerical value are consistent units of measurement across all medications. For example, one UOM rule removes trailing zeroes from the numerical value (e.g., 1 and not 1.0). Another UOM rule stores leading zeroes in the numerical value (e.g., 0.1 and not 0.1) and add commas for numbers greater than or equal to 1000 (e.g., 1,000). An additional UOM rule modifies the UOM string to ensure consistent capitalization and abbreviation. For example, CM is changed to cm, ML is changed to mL, centimeters is changed to cm, and """ is changed to inches.

UOM rules may also modify the string or numerical value depending on each element's value. For example, if the string is "G" and the numerical value is less than 1, the string may be converted to mg and the numerical value may be multiplied by 1000. In another example, if the numerical value is 1,000,000,000, the string may be modified to "Billion Units". In another example, if the string is "MU," and the numerical value is greater than or equal to 1,000, 000, then the string may be changed to "Billion Units" and the numerical value may be divided by 1,000,000. Inconsistencies between the numerical value and string may also be located and adjusted. For example, if the numerical value is 1,500,000 and the string is BU or Billion units, the numerical value may be given precedence such that the string is changed to Million Units.

UOM rules may also ensure proper spacing between strength numbers, unit volume, weight, and rates. For example, a UOM rule may ensure that there is a space between a strength number and units (e.g., 5 mL and not 5 mL). In another example, a make safe rule may ensure that numerical values are used in weights and rates (e.g., 50 mL/1 hr and not 50 mL/hr).

Accordingly, the UOM rules ensure that both the string and numerical value are consistent units of measurement across all medications.

Compression Rules

Compression rules provide for creating "compressed" values of drug attributes/elements and ensuring that drug strength values are created and stored within a 10-character limit. Compression rules include the removal of trailing and leading zeroes and spaces, the removal of spaces and dashes in fractions (e.g., 1-½ becomes 1½), and the abbreviation of common terms (e.g., in becomes", feet becomes ft, etc.).

Display Name Creation and Storage Rules

For each medication item, display name creation and storage rules provide for the creation and storage of generic and brand names for the medications that are displayed on display device 108. Such rules may utilize and refer to a spreadsheet file containing the relevant description/elements.

To provide an initial medication description that is used internally for applying and modifying rules and to obtain desired ordered medication descriptions, the following attributes may be concatenated with single space separators between each attribute:

(1) display name (generic or brand);

(2) display strength;

(3) display package strength;

(4) display package amount;

(5) display package size;

(6) display package description; and (7) display dosage form.

Each of the above attributes is based on additional attributes. For example, the display package size attribute may be a combination of the package size and the package size units from drug reference table 206. Further, a make safe procedure that ensures proper formatting, capitalization, spacing, etc. may be executed to create/determine each of the above attributes. For example, the following code may be utilized to create the display package size attribute:

```
DisplayPackageSize=MakeSafe(Str(PackageSize)+(PackageSize-
   Units)
```

In addition to the medication description that utilizes the above elements, the system may generate a different final medication description that is utilized to present the medication description on a display 108 to users. The final medication description may utilize the following elements, if available:

(1) the generic or brand display name;

(2) the display strength; and (3) the display dosage form.

Subsequent to the above three elements, the route information is inserted (if not already present). For example, if the medication is a nose/nasal spray, the delivery route "nasal" may be inserted into the final medication description. Similarly, the medication delivery route terms ophthalmic, otic, etc. may be inserted into the final medication description.

The final medication description may also be modified based on a sequence number for specific medications. For example, if a medication's sequence number matches a sequence number in a predefined table, the final description may be modified such that the medication name is followed by the display package amount and the display package size. For example, the final medication description from a predefined table may be "Lidocaine+DisplayPackageAmount+"in"+DisplayPackageSize+"_D5W"s.

The final medication description also includes a default strength and strength units that may be retrieved from a predefined table or based on additional attributes/elements.

Package Size Units Rules

For each medication item, the package size units is obtained and stored. During the obtaining process, formatting issues such as capitalization and abbreviations are corrected. For example, "TAB" may be changed to "Tab", "CAP" may be changed to "Cap", and "BAG" may be changed to "Bag". Additionally, predefined reference numbers may be converted to the corresponding package size units. For example, if a dosage form is "2", the package size may be converted to "mL".

If medication strength values are not provided or available in the drug reference table 206, package size rules add appropriate values. For example, if the generic or brand name of the medication contains the word "child", the medication strength may be specified as "PEDIATRIC".

Medication strength related elements may be adjusted based on independent information available to the system.

Accordingly, general independent strength related information is obtained and detailed information that is consistent therewith is determined. Relevant elements and fields may be compared to tables containing data and empty fields may be instantiated when a match is found. For example, a "make safe" procedure may be called that utilizes, compares, and confirms that the independent information is not inconsistent and may suggest or adopt additional strength related information based on the independent information. In a specific example, a make safe procedure may retrieve independent information that provides for a single component and time rate strength. The component and time rate strength information is converted into specific information for UOM strings. Thus, if the drug strength is *MM/*ML, then the unit is milliMoles per volume, and the appropriate strength related information such as strength units, volume units, display strength, etc. are instantiated with the appropriate information. In another example, a search for a sequence number in a table may be conducted and strength related values from the table into a drug object item may be instantiated if the sequence number is found.

Hospital Setup Tool

Substitutions and modifications of the medication description to ensure that the data is reconstructed accurately may be performed by clinical personnel using the hospital setup tool (HST)/display name manager tool 210 to create a set of accurate and consistent display names in the hospital formulary file 212.

Using the HST 210 and the data from drug reference table 206, pharmacy formulary 208, and the make safe rules, detailed medication information may be adjusted and modified. Thereafter, a final medication description is created for each medication to be stored in the formulary file 212 by appending various display-related elements to the display name in a software-controlled process based upon certain medication parameters.

Figure 3:
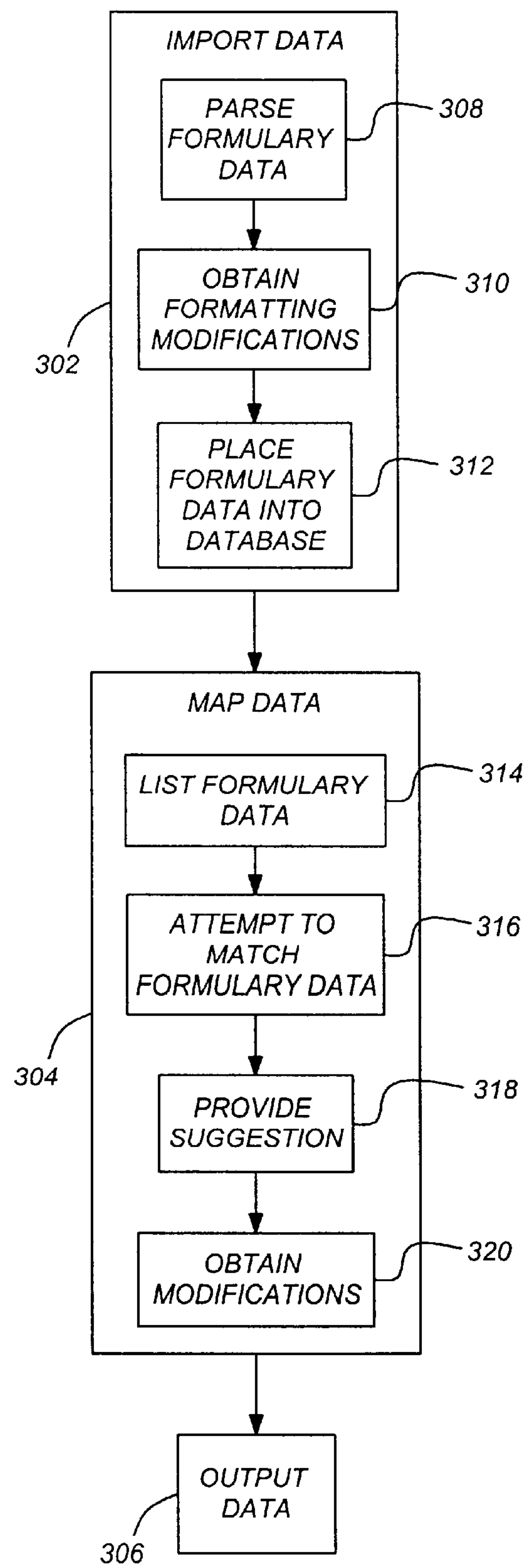
FIG. 3 is a flow chart illustrating the use of a hospital setup tool in accordance with one or more embodiments of the invention.

The hospital setup tool 210 provides for the verification of medication information utilized in a hospital formulary file 212. FIG. 3 is a flow chart illustrating the use of the hospital setup tool 210 in accordance with one or more embodiments of the invention. Three primary steps are involved in properly configuring and setting up the hospital formulary file 212 using the hospital setup tool 210: (1) importing formulary data 302; (2) mapping the formulary data; and (3) outputting the appropriate data into the hospital formulary file 212.

Importing pharmacy formulary data 208 is the first step 302 in setting up the hospital formulary file 212. The pharmacy formulary data 208 is usually comma separated data regarding medications offered by a pharmacy. The formulary data 208 is parsed at step 308 to find and correct any formatting errors. For example, the lengths of fields may be compared to maximum field lengths, dashes in NDC numbers may be removed, primary keys (e.g., row IDs) may be checked for uniqueness, and fields that should only contain numerals or letters are checked to ensure that only numerals or letters ate contained within them. A summary of the formatting errors that could not be automatically corrected may be presented to the user. The user may then have the option to manually correct the appropriate entries at step 310.

Once the formatting of the formulary data 208 has been modified (if necessary) and accepted by the user, the formulary data 208 is input into an internal database/table of the data referred to as the HST (hospital site table) site formulary. Once the data is input into the HST site formulary, the importing process 302 is complete.

Step 304 (mapping the data) provides the user with the option to map the pharmacy formulary data 208 to drug reference table data 206 and to view, modify, and accept the medication description. FIG. 4 illustrates the graphical user interface utilized in mapping step 304. At step 314, the formulary data from the pharmacy formulary 208 is listed (e.g., in column 402).

At step 316, the system attempts to match the pharmacy formulary data 208 with data from the drug reference table 206. If a match or potential match are found, the suggested drug reference table data 206 may be listed (e.g., in column 406) at step 318. Additionally, the information that the user elects to use to represent each element in the hospital formulary file 212 may be listed (i.e., in column 404). For ease of use, the individual elements of a medication description may be displayed in individual fields with each field of the pharmacy formulary data 208 adjacent to or in the same row of a corresponding element that is suggested. For example, the row indicating the dosage form 408 of a medication may indicate the type of field (i.e., "Dosage Form:") in one column, the pharmacy/site formulary dosage form in a second column 402 (i.e., "CAPSULE"), the item to be created in a third column (i.e., "Capsule, Hard, Soft, etc. (Cap . . . ") 404, and the suggestion/match in a fourth column 406 (i.e., "Capsule, Hard, Soft, etc. (Cap . . . ").

Once both the formulary data 208 and the suggestion from drug reference table 206 are displayed, modifications to the medication information may be obtained from the user at step 320. The user examines each medication using the graphical user interface (GUI) of FIG. 4. As described above, each column in the GUI comprises information relating to the medication. One column (e.g., column 404) is utilized to display the user's selection of the final representation and form of the data. The default information contained within the column 404 may be the suggestion/match from column 406. Further, certain elements may not be modifiable by the user (e.g., the generic or brand name). A user can elect to automatically transfer the text from column 402 (i.e., the pharmacy formulary data 208) or from column 406 (i.e., the suggested/matched data 206) into column 404.

The user can manually modify the data in column 404 by deleting, copying, typing, etc. directly into the fields in column 404. If data in column 404 is changed by the user, upon the user electing to save the data, the medication description data 410 may be modified to reflect the changes. Accordingly, the medication description 410 is based on the elements (from column 404) used to represent the medication. Further, the medication description 410 can be modified directly to add desired information or notes to be displayed (e.g., "MUST BE ORAL"). The medication description 410 of column 404 is the description that will be displayed and utilized by users of the system. Accordingly, the description should be consistent across multiple sites. By providing the suggestion from column 406 and the ability for a user to modify medication information, the appropriate medication and a consistent display/reference to the medication is utilized.

The GUI of FIG. 4 may also provide flags or color coding to indicate when changes have been made or when particular fields need to be confirmed/checked. For example, if the user modifies a field in column 404 that differs from the suggestion in column 406, a flag may be displayed adjacent to the row containing the modified entry. Alternatively, the changed field may be highlighted or displayed in a different color.

If important information is changed by the user at step 320, the user may be prompted to confirm the change and/or to confirm whether the updated or original information should be utilized when clinical checks are conducted. In other words, the user is given the option of whether or not to link to the remaining data (that is not hidden from the user) for the medication as suggested in column 406.

Once linked, the data for the medication indicated in column 406 is utilized in clinical checks. As described above, clinical checks confirm that the administration of medication does not violate a series of rules and provide warnings to users when a rule violation occurs. For example, if a nurse attempts to administer secobarbital by injection, a link to the route information in column 406 may enable the display of a warning to the nurse to administer the prescription orally. Further, information related to secobarbital but not displayed in the GUI may also be utilized.

Linking may be desirable because some clinical rules may need clinical information for the linked drug even if a field has been changed. For example, if the package size is changed or a percentage value is changed, the information for the medication may still be utilized in clinical checks. Alternatively, linking may not be desirable if the medication has been significantly changed in column 404 from that listed in column 406. For example, if the user is listing a banana as a medication in column 404 and the only suggestion that is found is for opium, the user would likely not want to link the banana to opium such that clinical checks will use the attributes for opium when a banana is prescribed. In another example, suppose secobarbital is traditionally administered orally but the hospital is utilizing a new method of crushing the pill, mixing the pill with intravenous fluid (IV) and administering the mixture through intravenously. In such a situation, the pharmacist still needs to modify the information in column 404. However, the pharmacist may still desire to link the new mixture to the original secobarbital record in column 406 for use in clinical checks. Accordingly, the pharmacist is provided the option of linking the medication to the original medication or match listed in column 406.

Step 316 attempts to match the site formulary data 208 with drug reference table data 206. Once a match is found, column 406 displays the resulting match. If the displayed information in column 406 is not the appropriate medication/information, a user may directly enter the information and/or search for the appropriate medication/information by selecting the find button 412. In response, a GUI for conducting a query of the drug reference table 206 information may be utilized to search and retrieve medication information. Additionally, a "smart" search may be conducted that provides the ability to locate the "best" match based on the dosage form, brand name, dosage strength, and/or generic name. Using a smart search, if an exact match cannot be found, the GUI displays a list of those medications that contain the most matches. The user may select one of the listed medications to retrieve the related medication information. Once selected, the retrieved information is displayed in column 406 for the user to work with and modify if desired.

If the desired medication is not suggested (or cannot be found by the user), the approval of the formulary information in column 402 may be postponed until a later time by selecting the postpone button 414.

The system may also maintain a full audit trail that tracks any changes made in column 404, who made the changes, what the user was viewing when the change was made, when the changes were made, what questions were answered (and the responses to the questions), and other relevant auditing information. Accordingly, when mistakes are encountered, the audit trail may be viewed to determine the relevant information about the user and the actions taken when the mistake was entered into the system.

Once the user using the GUI of FIG. 4 has verified all of the medications, a final verification screen provides the user with the option to save and/or export the validated medication data. Accordingly, once the medications have all been verified, mapping step 304 is complete and the data may be output to the hospital formulary file 212 at step 320. Further, once the user has selected to save/output the data, various formatting checks may be performed once again. For example, the system may ensure that primary keys are unique, field lengths are appropriate, and characters and numerals are utilized appropriately. Once saved/output to the HFF 212, the HFF 212 may be utilized and accessed to retrieve medication information and to obtain the medication description to be displayed/utilized throughout the site/hospital.

Accordingly, the medication description management, make safe rules, data reconstruction, and hospital setup tool components are utilized to provide accurate medication description content and appearance.

Graphical User Interface

Once the medication elements, attributes, and descriptions have been made "safe", and transferred into HFF 212, a graphical user interface (GUI) provides for the display of the relevant information in various formats and screens/areas.

GUI display areas may include a components display and a medications display. The components display may include various tabs for listing the components, entering observations, and entering the administration of the component. The medications display may include a scheduled medications screen, a PRN screen, an IV screen, an all screen, a floorstock screen, and a formulary screen.

To ensure that the medication orders properly and consistently identify the medication and comply with the five patient rights (i.e., right patient, right drug, right dose, right route of administration, and right time), the elements and attributes from HFF 212 are utilized and the medication description utilized remains consistent throughout all of the display screens. Further additional compliance checks may be performed using the elements and attributes from HFF 212 to protect against medication errors.

Accordingly, medications on each screen are displayed using three columns. The first column contains either the generic or brand final display medication description depending on the user's selection. Column 2 comprises either the display package size, display package strength, or display strength. Column 3 comprises either the display package description, display dosage form, or an empty field. Using this three-columnar format, relevant consistent medication information that provides the ability to properly and completely identify the medication is displayed and utilized by the user. For any patient order, the medication displayed always provides the order give amount, the order give units, and the order display name (created using the final display medication description). Additionally, a pop-up window containing the entire medication description may be displayed when the display cursor is placed over any listed medication/order.

For component orders, a components tab/screen with each component and the amount of the component is provided.

Component orders are orders wherein various components are added together to create a complete product. For example, a component order may call for the use of eight (8) different components to utilize in an intravenous solution (e.g., 600 mL Dextrose in Water, 400 mL Sterile Water, 250 mL Fat Emulsions 10%, 40 mEq KCI, 4.65 mEq CaGlucon, 8 mEq MagSulf, 10 mM Kphos, and NaPH).

FIG. 5 illustrates a scheduled medication GUI screen in accordance with one or more embodiments of the invention. A scheduled medication list/screen identifies dose times/time due of the medication (using military time) 502, the name of the medication (using the consistent medication description) 504, and the last time the medication was administered (if any) 506. Additionally, the screen may indicate whether the scheduled medication is for a confirmed and active order and may provide a list of previously administered medications. When a nurse elects to administer a particular listed/scheduled medication, details of the medication are displayed. For example, when a nurse selects a particular prescription for administration, the route of the administration (e.g., IV) is displayed to the nurse.

The PRN screen provides for medications that are pro re nata (given on demand). The PRN medication is listed with the consistent medication description followed by the last time the PRN medication was administered in a separate column. The PRN screen follows the same guidelines utilized for the scheduled medications screen.

The IV screen displays all of the IV medication orders for a given patient. Each medication listed in the IV screen is also accompanied by the strength and rate for administering the medication intravenously.

The all medications screen/list provides details on all patient orders and medications (IV, PRN, or otherwise) for a given patient. Each medication/patient order is listed with the appropriate strength, dosage, rate, etc. related information as provided on the other screens of the GUI. For example, the time the medication was last administered and the order state (e.g., active, on hold, future, expired, etc.) may be displayed adjacent to PRN and scheduled medications.

The floorstock screen provides a listing of the patient orders/scheduled medications that are retrieved from the floorstock where the patient is located. For example, Tylenol may be retrieved from the floorstock and administered to the patient.

The formulary screen provides a listing of the patient orders/scheduled medications that are obtained/retrieved from the hospital's pharmacy. Such medications can include pain medications such as Morphine or tablets of antibiotics such as Keflex.

Once the nurse or person administering the medication selects a medication from one of the above screens, detailed information regarding the medication is displayed to the user. The detailed information allows the administer of the medication to confirm or delete one, some, or all of the medications as they are administered to the patient. A confirmation screen may present additional information such as the time the medication was administered, the name of the administer of the medication, and a co-signature (if required for the medication). Additionally, the confirmation or detailed medication screen may indicate the dose amount, dose unit, rate, route units, and route.

Conclusion

This concludes the description of one or more embodiments of the invention. The following describes some alternative embodiments for accomplishing the present invention. For example, any type of computer, such as a mainframe, minicomputer, pen tablet, CE device, or personal computer, or computer configuration, such as a time-sharing mainframe, local area network, or standalone personal computer, could be used with the present invention. In summary, embodiments of the invention provide the ability to consistently display access, and utilize medication information including medication descriptions.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A computer-implemented method for displaying consistent medication information comprising:

creating an electronic drug reference table comprised of medication information;

receiving an electronic formulary comprising formulary medication information;

creating an electronic formulary file comprising medication information content, wherein the medication information content comprises a combination of the electronic drug reference table and the electronic formulary; and displaying the medication information content.

2. The method of claim 1, wherein the medication information is obtained from one or more drug manufacturers.

3. The method of claim 1 wherein the medication information content is displayed at a time of administration of medication.

4. The method of claim 1 wherein the medication information content is displayed at a time of prescribing medication.

5. The method of claim 1 wherein the medication information content is displayed at a time of computerized prescription order entry.

6. The method of claim 1 wherein the electronic formulary is received from a hospital.

7. The method of claim 1 wherein the electronic formulary is received from a pharmacy.

8. The method of claim 1 wherein the creating of the electronic formulary file further comprises applying one or more rules that ensure the medication information content and appearance is consistent and accurate.

9. The method of claim 1 wherein the creating comprises providing a hospital setup tool that enables a user to modify and approve medication information content to be placed into the electronic formulary file.

10. The method of claim 1 wherein the medication information content displayed is based on patient orders for a specified patient.

11. An apparatus for displaying consistent medication information in a computer system comprising:

means for creating an electronic drug reference table comprised of medication information;

means for receiving an electronic formulary comprising formulary medication information;

means for creating an electronic formulary file comprising medication information content, wherein the medication information content comprises a combination of the electronic drug reference table and the electronic formulary; and means for displaying the medication information content.

12. The apparatus of claim 11, wherein the medication information is obtained from one or more drug manufacturers.

13. The apparatus of claim 11 wherein the medication information content is displayed at a time of administration of medication.

14. The apparatus of claim 11 wherein the medication information content is displayed at a time of prescribing medication.

15. The apparatus of claim 11 wherein the medication information content is displayed at a time of computerized prescription order entry.

16. The apparatus of claim 11 wherein the electronic formulary is received from a hospital.

17. The apparatus of claim 11 wherein the electronic formulary is received from a pharmacy.

18. The apparatus of claim 11 wherein the means for creating the electronic formulary file comprises means for applying one or more rules that ensure the medication information content and appearance is consistent and accurate.

19. The apparatus of claim 11 wherein the means for creating comprise means for providing a hospital setup tool that enables a user to modify and approve medication information content to be placed into the electronic formulary file.

20. The apparatus of claim 11 wherein the medication information content displayed is based on patient orders for a specified patient.

21. An article of manufacture comprising a program storage medium readable by a computer and embodying one or more instructions executable by the computer to perform a method for displaying consistent medication information, the method comprising:

creating an electronic drug reference table comprised of medication information;

receiving an electronic formulary comprising formulary medication information;

creating an electronic formulary file comprising medication information content, wherein the medication information content comprises a combination of the electronic drug reference table and the electronic formulary; and displaying the medication information content.

22. The article of manufacture of claim 21, wherein the medication information is obtained from one or more drug manufacturers.

23. The article of manufacture of claim 21 wherein the medication information content is displayed at a time of administration of medication.

24. The article of manufacture of claim 21 wherein the medication information content is displayed at a time of prescribing medication.

25. The article of manufacture of claim 21 wherein the medication information content is displayed at a time of computerized prescription order entry.

26. The article of manufacture of claim 21 wherein the electronic formulary is received from a hospital.

27. The article of manufacture of claim 21 wherein the electronic formulary is received from a pharmacy.

28. The article of manufacture of claim 21 wherein the creating of the electronic formulary file further comprises applying one or more rules that ensure the medication information content and appearance is consistent and accurate.

29. The article of manufacture of claim 21 wherein the creating comprises providing a hospital setup tool that enables a user to modify and approve medication information content to be placed into the electronic formulary file.

30. The article of manufacture of claim 21 wherein the medication information content displayed is based on patient orders for a specified patient.

* * * * *

UNITED STATES PATENT AND TRADEMARK OFFICE

CERTIFICATE OF CORRECTION

PATENT NO. : 6,694,334 B2
DATED : February 17, 2004
INVENTOR(S) : Donna B. DuLong et al.

It is certified that error appears in the above-identified patent and that said Letters Patent is hereby corrected as shown below:

Title page,
Item [56], References Cited, U.S. PATENT DOCUMENTS, insert, -- 5,367,555 11/1994 Isoyama….379/38 --.
OTHER PUBLICATIONS, insert, -- Microsoft TechNet, “Architectural Design: A Scalable, Highly Available Business Object Architecture” http://www.microsoft.com/technet/ecommerce/ObjArchi.asp?a=printable, July 2000, pp. 1- 12. --

Signed and Sealed this

Sixth Day of July, 2004

JON W. DUDAS
*Acting Director of the United States Patent and Trademark Office*